United States Patent
Huebner et al.

(10) Patent No.: US 8,262,707 B2
(45) Date of Patent: Sep. 11, 2012

(54) PERIARTICULAR BONE PLATE WITH BIPLANAR OFFSET HEAD MEMBER

(75) Inventors: Dave Huebner, Kearney, NE (US);
George Haidukewych, Tampa, FL (US);
G. Mark Lindsay, Fort Wayne, IN (US);
Craig S. Tsukayama, Fort Wayne, IN (US); Roy Sanders, Tampa, FL (US)

(73) Assignee: Biomet C.V., Gibraltar (GI)

( * ) Notice: Subject to any disclaimer, the term of this patent is extended or adjusted under 35 U.S.C. 154(b) by 815 days.

(21) Appl. No.: 12/183,115

(22) Filed: Jul. 31, 2008

(65) Prior Publication Data
US 2010/0030276 A1  Feb. 4, 2010

(51) Int. Cl.
*A61B 17/80* (2006.01)
(52) U.S. Cl. .................. 606/280; 606/286; 606/291
(58) Field of Classification Search .............. 606/280, 606/283, 284, 286
See application file for complete search history.

(56) References Cited

U.S. PATENT DOCUMENTS

| | | | |
|---|---|---|---|
| 5,938,664 | A | 8/1999 | Winquist et al. |
| 6,093,201 | A | 7/2000 | Cooper et al. |
| 6,355,045 | B1 | 3/2002 | Gundlapalli et al. |
| 6,623,486 | B1 | 9/2003 | Weaver et al. |
| 7,128,744 | B2 | 10/2006 | Weaver et al. |
| 7,179,260 | B2 | 2/2007 | Gerlach et al. |
| 2004/0030339 | A1* | 2/2004 | Wack et al. ............ 606/69 |
| 2004/0059335 | A1 | 3/2004 | Weaver et al. |
| 2004/0116930 | A1 | 6/2004 | O'Driscoll et al. |
| 2004/0186477 | A1 | 9/2004 | Winquist et al. |
| 2005/0010226 | A1 | 1/2005 | Grady, Jr. et al. |
| 2005/0070904 | A1 | 3/2005 | Gerlach et al. |
| 2005/0080421 | A1 | 4/2005 | Weaver et al. |
| 2005/0107796 | A1 | 5/2005 | Gerlach et al. |
| 2005/0261688 | A1 | 11/2005 | Grady, Jr. et al. |
| 2006/0173458 | A1 | 8/2006 | Forstein et al. |
| 2007/0088360 | A1 | 4/2007 | Orbay et al. |
| 2007/0173843 | A1 | 7/2007 | Matityahu |

FOREIGN PATENT DOCUMENTS

| | | |
|---|---|---|
| EP | 1250892 | 10/2002 |
| EP | 1211992 | 1/2004 |
| WO | WO 01/82809 | 11/2001 |

OTHER PUBLICATIONS

AxSOS™, Locking Plate System Brochure, Literature No. 982295.
Synthes, 4.5 mm LCP® Proximal Tibia Plate, Stainless Steel and Titanium Technique Guide, GP2079-E, Rev. 2/05, J4053-E.
Zimmer®, Periarticular Proximal Tibial Locking Plates, 2005.
AxSOS™, Locking Plate System Brochure, (2007) Literature No. 982295 (submitted with enlarged last page to better show publication date).

* cited by examiner

*Primary Examiner* — Nicholas Woodall
(74) *Attorney, Agent, or Firm* — Gordon & Jacobson, PC

(57) ABSTRACT

A periarticular bone plate for the internal fixation of a fractured, proximal tibia of a surgical patient includes a shaft member connected to a head member, a top surface, a bottom surface, a posterior edge, an anterior edge and a plurality of holes extending between the top and bottom surfaces for receiving fasteners for attaching the plate to the bone. The head member is offset relative to the shaft member in each of a frontal and sagittal planes of the proximal tibia.

19 Claims, 5 Drawing Sheets

PERIARTICULAR BONE PLATE WITH BIPLANAR OFFSET HEAD MEMBER

BACKGROUND OF THE INVENTION

1. Field of the Invention

This invention relates broadly to surgical devices for the internal fixation of fractured bones, and more particularly to bone plates.

2. State of the Art

Currently available bone plates for the proximal tibia have a head portion extending from a shaft portion, wherein the head portion is offset from the shaft portion in the frontal plane. However, others have failed to recognize that this offset does not completely accommodate the anatomy, and that the anterior edge of the plate may extend too far anteriorly and not seat properly on the proximal tibia. For example, the Gerdy's tubercle region of the proximal tibia presents a prominence that may prevent the plate from fully seating on the bone. Furthermore, the prominence of plate and the associated fasteners in the proximal anterior direction could possibly contribute to irritation of soft tissues, particularly the iliotibial tract connected to Gerdy's tubercle, and consequently patient discomfort.

SUMMARY OF THE INVENTION

A periarticular bone plate for the internal fixation of a fractured proximal tibia of a patient includes a shaft portion connected to a head portion, a bone contacting bottom surface, and an opposite top surface. The shaft portion includes a plurality of holes extending between the top and bottom surfaces for receiving fasteners for attaching the plate to the bone. The head portion is oriented transverse to the shaft portion and defines a plurality of holes configured in proximal and distal rows extending between the top and bottom surfaces for receiving fasteners for attaching the plate to the bone. The head portion is offset relative to portions of the shaft portion in each of two planes; i.e., both the frontal and parasagittal planes when the bottom surface of the plate is positioned on the frontal surface of the proximal tibia. The shaft portion includes a proximal portion which is laterally straight and which has a concave bottom surface and a distal portion with laterally straight sides and a flat bottom surface. The proximal and distal shaft portions define an angle centered along the longitudinal axis of the plate. The angle is approximately 168° to 173°, and the angle center is positioned about in a range of 42 mm to 50 mm from the proximal row of holes in the head portion. The center of the anterior hole in the head portion is displaced from a line parallel to the anterior side of the straight distal portion of the shaft by about in the range of 10 mm to 12 mm. The amount of frontal offset may vary between about 14 mm and 20 mm.

According to a preferred aspect of the bone plate, at least one of the holes is internally threaded for receiving a locking fastener having a threaded head.

According to another preferred aspect of the bone plate, the head portion includes two rows of at least three holes each, each of the holes being formed by the plate itself to receive a locking fastener.

According to another preferred aspect of the bone plate, the bone plate includes at least one multifunctional hole in a proximal edge of the head portion for either one of guiding a K-wire and attaching a suture. The multifunctional hole includes a first path, e.g. bore, sized to guide a K-wire and having a first axis extending between the top and bottom surfaces. The multifunctional hole also includes a second path having a second axis extending inward from the proximal edge and under the top surface, such that the first and second axes intersect.

Additional objects and advantages of the invention will become apparent to those skilled in the art upon reference to the detailed description taken in conjunction with the provided figures.

DETAILED DESCRIPTION OF THE PREFERRED EMBODIMENTS

Figures 1, 2:
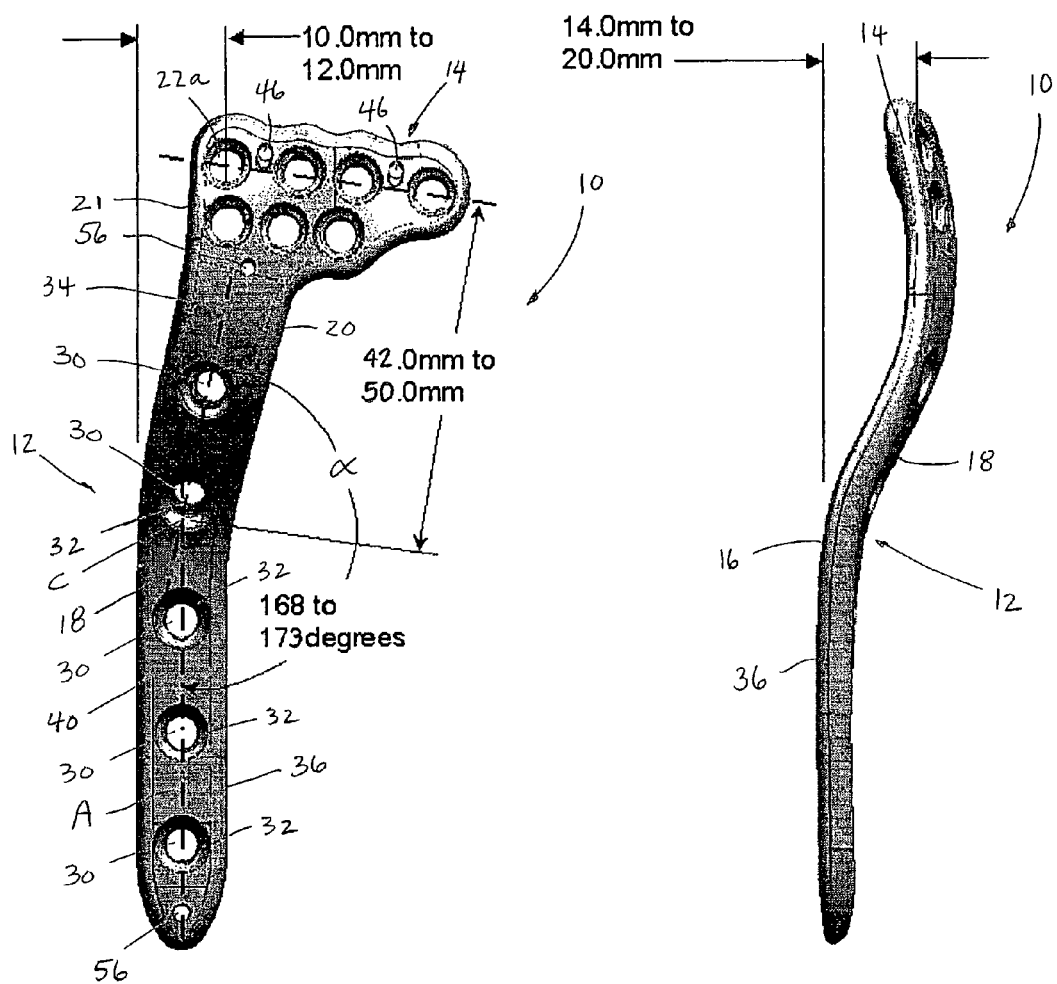
FIG. 1 is a sagittal plane view of a bone plate according to the invention, illustrating the offset of the head portion relative to the distal shaft portion.
FIG. 2 is a front plane view of a bone plate according to the invention, illustrating the offset of the head portion relative to the distal shaft portion.

Turning now to FIGS. 1 and 2, a periarticular bone plate 10 for the internal fixation of a fractured proximal tibia of a patient is shown. The plate 10 is preferably made from titanium, but can also be made of other suitable metals including stainless steel and cobalt chrome. Plate 10 includes a shaft portion 12 unitary with a head portion 14, a bone contacting bottom surface 16, and an opposite top surface 18. The head portion 14 is oriented transverse to the shaft portion 12 and extends on the posterior side 20 of the shaft portion 12, but not on the anterior side 21.

Referring to FIG. 1 through 4, the head portion 14 defines a plurality of screw holes 22 extending between the top and bottom surfaces 16, 18 for receiving fasteners, described below, for attaching the plate 10 to bone. As seen best in FIG. 4, the screw holes 22 are preferably internally threaded such that the threads 23 define respective screw hole axes, e.g., $A_{H1}$ and $A_{H2}$. Such internally threaded screw holes 22 secure fasteners having threaded heads to the plate 10 along the respective axes of the screw holes. Additionally or alternatively, the screw holes 22 may each include a surrounding recess 24 to accept the head of a locking or non-locking multidirectional fastener. Such recesses 24 maybe spherically or non-spherically curved. Screw holes 22 are configured in a proximal row 28 and a distal row 30 oriented parallel to each other but offset relative to each other. The proximal row 28 preferably includes at least three screw holes 22 and more preferably four screw holes 22. The distal row 30 preferably includes at least three screw holes 22. The offset of the rows 28, 30 permits a 'stacked raft' subchondral support of the femoral load on the joint.

Referring to FIGS. 1 and 2, the shaft portion 12 includes a plurality of screw holes 30 extending between the top and bottom surfaces 16, 18 for receiving fasteners, described below, for attaching the plate 10 to the proximal tibia. The screw holes 30 are preferably internally threaded such that the threads define respective screw hole axes. Such internally threaded screw holes 30 secure a fastener having a threaded head to the plate along the axis of the screw hole. Additionally or alternatively, the screw holes 30 each may include a surrounding recess 32 to accept the head of a locking fastener or a non-locking multidirectional fastener.

The shaft portion 12 includes a proximal portion 34 and a distal portion 36. The proximal portion 34 is laterally straight (straight when projected on a parasagittal plane) and longitudinally curved (curved out of the same parasagittal plane as the distal portion 36). The distal portion 36 is laterally and longitudinally straight. When projected onto a parasagittal plane, the proximal and distal portions 34, 36 are angled relative to each other at an angle α centered along the longitudinal axis A of the plate 10. The angle α is approximately 168° to 173°, and the center C of angle α is positioned about in a range of 42 mm to 50 mm from the proximal row 28 of holes in the head portion 14. The center of the anterior hole 22a (the proximalmost screw hole) in the head portion 14 is displaced from the anterior side 40 of the distal portion 36 of the shaft portion 12 by about in the range of 10 mm to 12 mm. Due the longitudinally curve of the proximal portion 34, head portion 14 does not extend in the same parasagittal plane as the distal shaft portion 36. More specifically, the head portion 14 is frontally offset relative to the distal shaft portion 36 by about in the range of 14 mm and 20 mm. The ranges in dimensions, displacements, and offsets are provided for different plates to accommodate proximal tibias of different sizes and anatomical contours.

Figure 3:
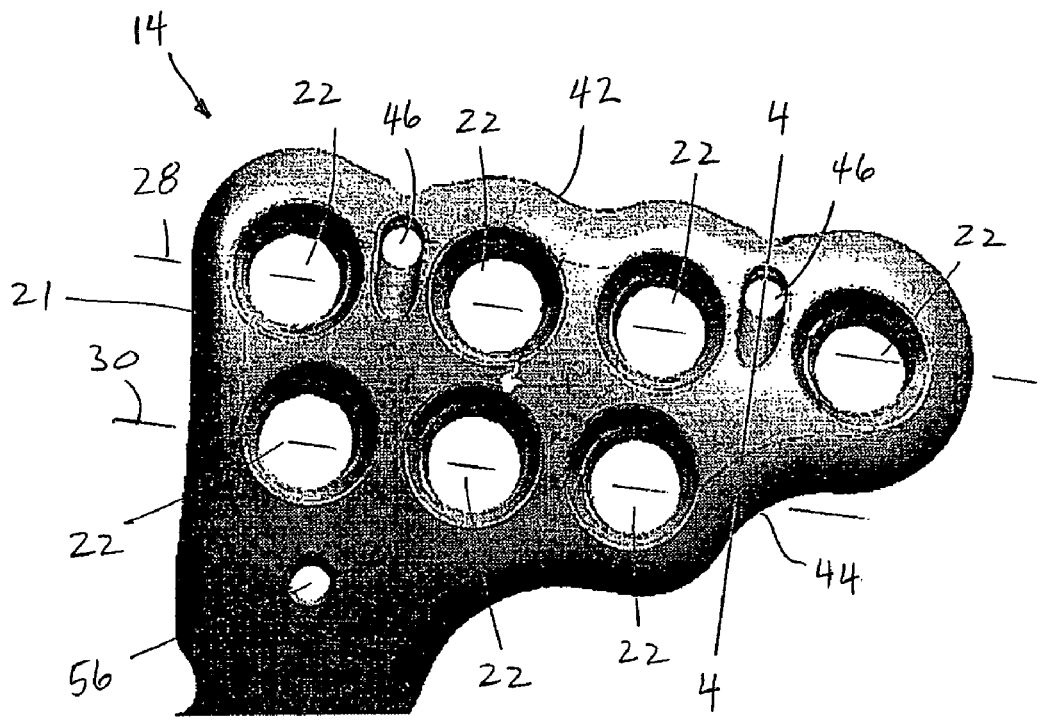
FIG. 3 is an enlarged view of the head portion of the bone plate according to the invention.

Referring to FIG. 3, the head portion 14 includes a scalloped contour along the proximal edge 42 about the proximal row 28 of screw holes and along the posterior side 44 about the posterior screw holes 22 of the proximal and distal rows 28, 30. This curved shape reduces the profile and minimizes the material of the plate to reduce tissue irritation. The head portion 14 is straight along the anterior side 21.

Figure 4:
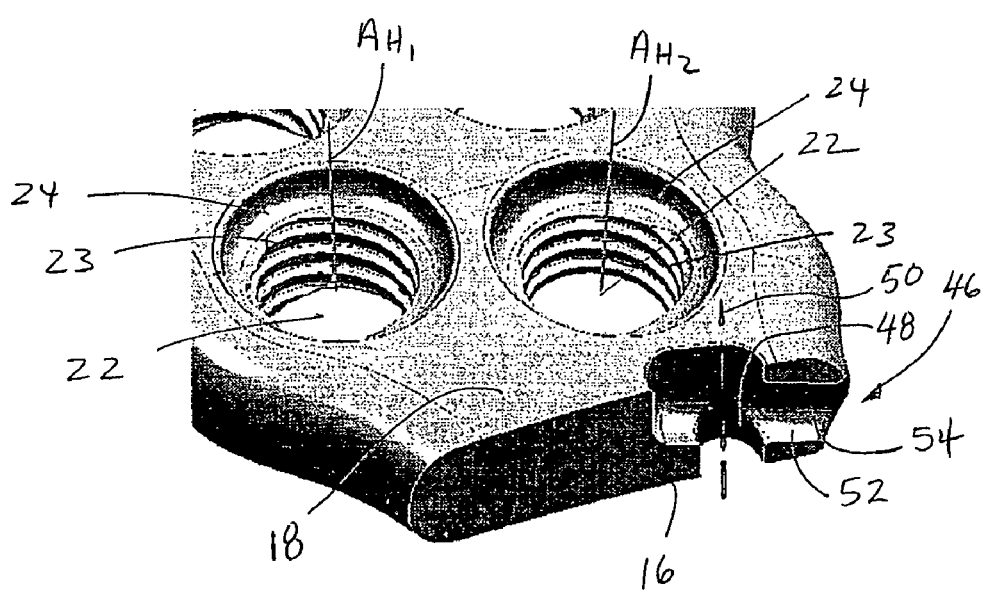
FIG. 4 is a section through line 4-4 in FIG. 3.

Referring to FIGS. 1, 3 and 4, the head portion 14 is also preferably provided with at least one multifunctional 46, with two such holes shown. Multifunctional hole 46 is structured to both guide a K-wire and accept a suture. The multifunctional hole 46 includes a first path, e.g. bore, 48 sized to guide and constrain (±3°) a K-wire along a first axis 50 extending through the top and bottom surfaces 16, 18. Hole 46 also includes a second path 52 extending inward from the proximal edge 42 and entirely between the top and bottom surfaces 16, 18 and having a second axis 54. Alternatively, the second path 52 may be defined as a recess in the bottom surface 16 extending inward from the proximal edge 42. The first and second axes 50, 54 intersect. A suture with needle can be inserted through the second path 52 and up and out the first path 48 (or in the reverse direction) to allow the repair of a surgically detached or torn meniscus after the plate is applied to the proximal tibia. Standard K-wire holes 56 are preferably also provided at the distal end of the shaft portion 12 and the intersection of the shaft and head portions 12, 14 for temporary fixation of the plate 10 on the bone.

Figure 5:
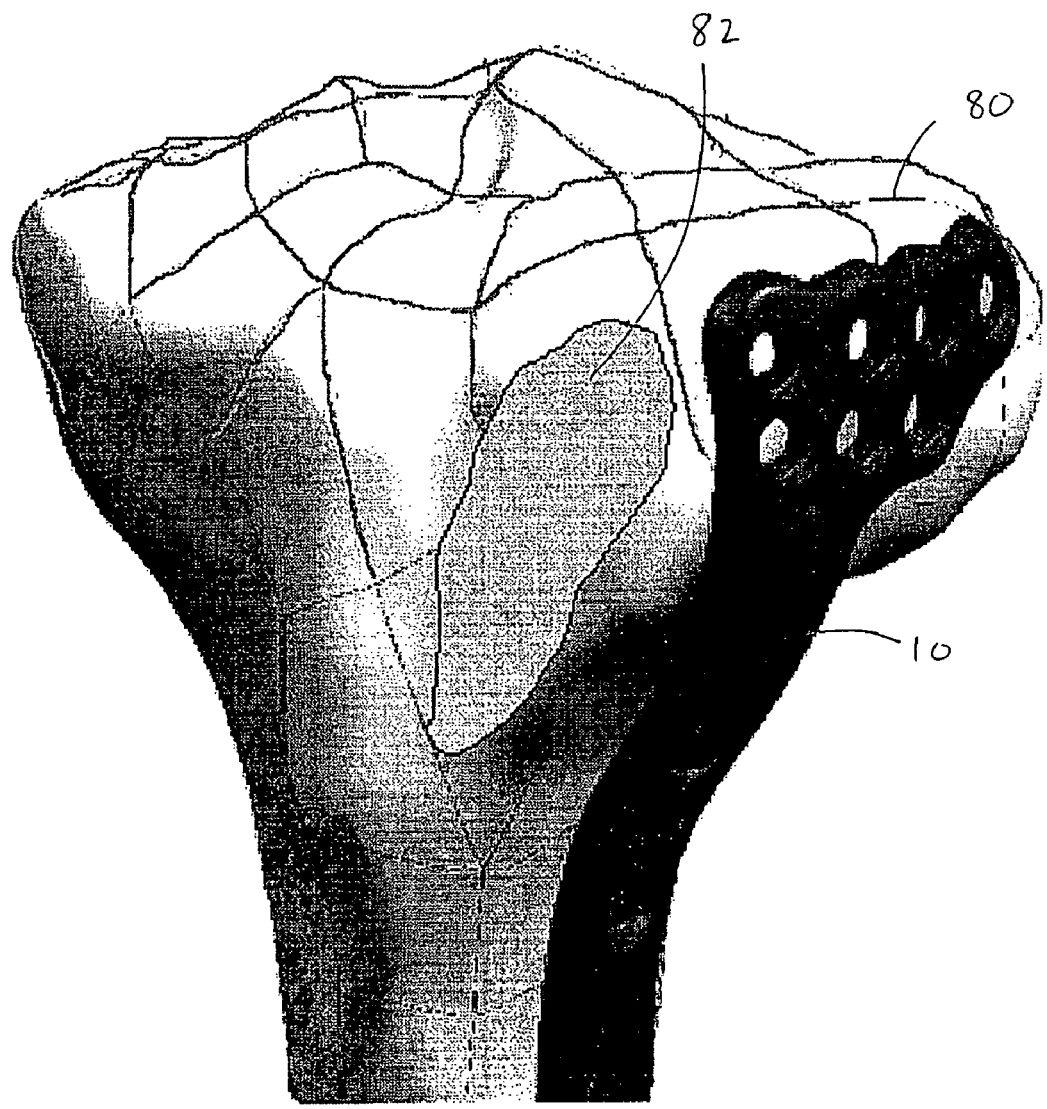
FIG. 5 shows the bone plate of the invention located on the proximal tibia.

Referring to FIG. 5, when the plate 10 is positioned on the proximal tibia bone 80 of patient, the plate conforms substantially better to the bone and the soft tissue attached thereto. The angular offset of the proximal shaft portion 34 relative to the distal shaft portion 36 accommodates the natural 10°-12° degree slope of the proximal tibia. Thus, the transverse orientation of the head portion 14 is shifted to a more posterior position to allow a better buttressing of a fractured condyle (anti-glide interference effect of the apex), the most common fracture of the tibial plateau. This also allows for less prominence of the plate anteriorly, in the region of Gerdy's tubercle 82, where soft tissue irritation is common. The plate also facilitates closure of the iliotibial band (attached to Gerdy's tubercle) over the plate and fasteners by reducing bulk in this area. As such, the plate 10 provides better proximal fixation options, suture fixation simplicity, stacked raft locking capability, and low profile, soft tissue friendly contours.

As indicated above, several types of fasteners can be used in conjunction with the plate. Turning now to FIGS. 6 through 9, exemplary fasteners for the screw holes 22, 30 are now described. Generally, the fasteners include a shank portion for engagement into the bone, wherein the shank portion may have one of a cortical thread, a cancellous thread, a non-threaded portion and combinations thereof. Each fastener type further includes a head portion for engagement with the fastener hole, wherein the head portion may have one of a fixed angle locking head, a non-locking compression head and a multidirectional locking head.

Figure 6:
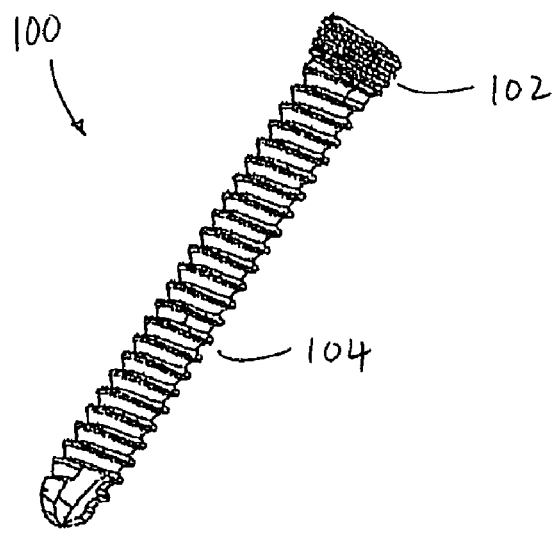
FIG. 6 is a perspective view of a fixed angle locking fastener with cortical threads for use with the bone plate of the invention.
Figure 7:
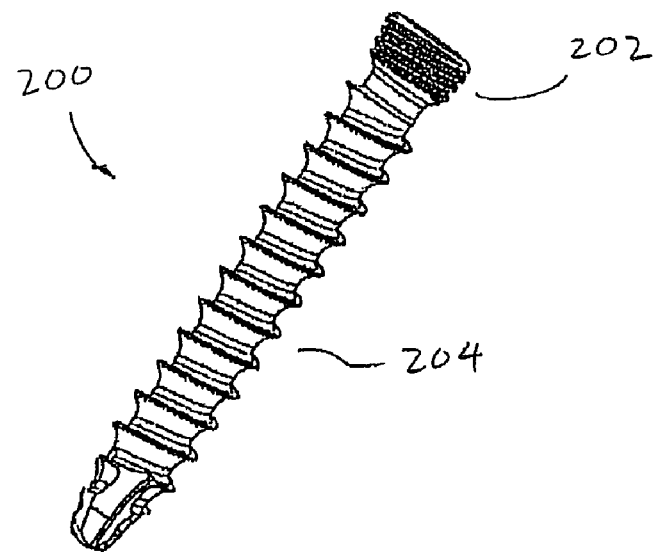
FIG. 7 is a perspective view of a fixed angle locking fastener with cancellous threads for use with the bone plate of the invention.

FIG. 6 is a side view of a fixed angle locking screw 100, which includes a tapered threaded head 102 having a driver recess (not shown), and a threaded shaft 104. The threads on the shaft having a pitch adapted for engaging cortical bone. Screw 100 may be inserted and locked into a tapered, threaded hole of a bone plate at a fixed angle predetermined by the thread axis. FIG. 7 is a side view of a fixed angle locking screw 200, substantially similar to screw 100, but wherein the threads of shaft 204 have a relatively larger pitch adapted for engaging cancellous bone.

Figure 8:
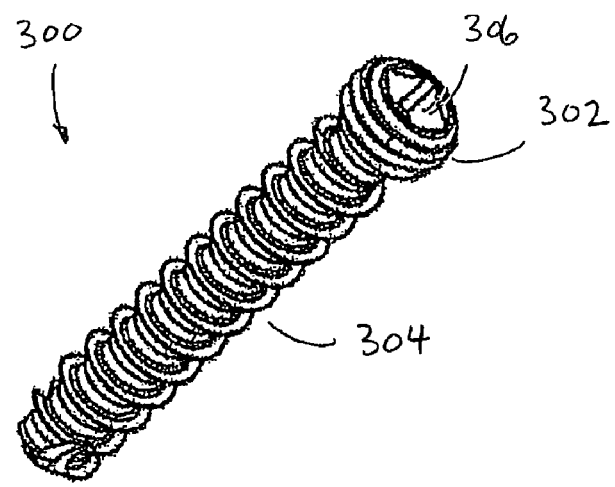
FIG. 8 is a perspective view of a multidirectional locking fastener for use with the bone plate of the invention.

FIG. 8 is a side view of a multidirectional locking screw 300 having a head 302 with a square drive recess 306, and a shaft 304. The screw 300 may be locked into the plate, such that a screw axis forms an angle in the range of 0-15 degrees with the thread axis of the hole. Screw 300 may be formed from an alloy that is significantly harder than the plate material. For example, where the plate 10 is constructed of titanium alloy, the screw 300 is made from cobalt-chrome. Such a multidirectional locking screw is described in detail in U.S. Pub. No. 20070088360A1, which is hereby incorporated by reference herein in its entirety.

For the fastener embodiments 100, 200, and 300, the shaft can alternatively be smooth along all or a portion of its length.

Figure 9:
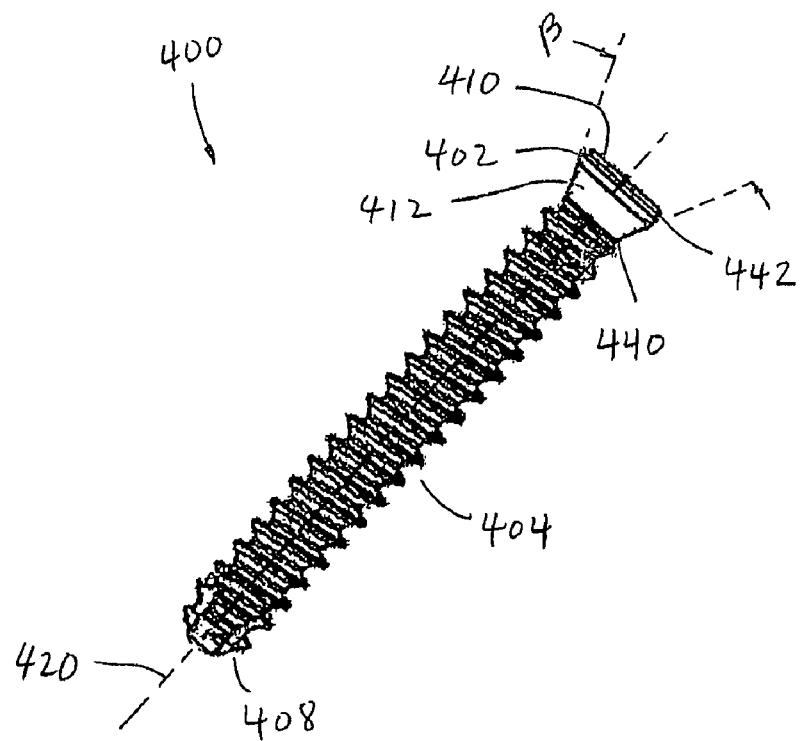
FIG. 9 is a perspective view of a compressive fastener for use with the bone plate of the invention.

FIG. 9 is a multidirectional compression fastener 400, also called screw 400. Screw 400 includes a threaded shaft 404 and a distal tip 408. Screw 400 further includes a head 402 having a proximal face 410 with a square drive recess, although other drive recess configurations are possible. Head 402 includes a smooth, frustoconical portion 412 having a small diameter end 440 attached to the body 404 and a large diameter end 442 forming a peripheral edge of proximal face 410. Frustoconical portion 412 has an included angle β centered on a screw axis 420. Threads of screw shaft 404 may be either cancellous or cortical, and may optionally be formed along only a portion of the length of the shaft 404. Other multidirectional and unidirectional compression fasteners can also be used.

There have been described and illustrated herein embodiments of a bone plate for the proximal tibia and fasteners therefor such that a system is presented. While particular embodiments and dimensions of the invention have been described as such are believed to provide a plate with the best anatomical contouring, proximal fixation options, and low profile, it is appreciated that the term 'approximately' with respect to an angle is intended to include other angles outside the stated range that when used in association with the plate provide equivalent structure and/or functionality, and the term 'about' with respect to dimensions is intended to include other dimensions within ±10%, provided such dimensions when used in association with the plate provide equivalent structure and/or functionality. It is therefore not intended that the invention be limited to the particular embodiment described, as it is intended that the invention be as broad in scope as the art will allow and that the specification be read likewise. It will therefore be appreciated by those skilled in the art that yet other modifications could be made to the provided invention without deviating from its spirit and scope as claimed.

What is claimed is:

1. A periarticular bone plate for use with bone fasteners for stabilizing a fracture of the proximal tibia, comprising:
   a shaft portion and a head portion unitary with the shaft portion, the shaft and head portions having a bone contacting bottom surface, an opposite top surface, an anterior side, and a posterior side,
   said head portion defining a first plurality of screw holes configured in a proximal row of at least three screw holes and a distal row of at least three screw holes, and said shaft portion defining a second plurality of screw holes longitudinally displaced relative to a longitudinal axis of said shaft, said first and second plurality of screw holes screw holes extending between said top and bottom surfaces for receiving fasteners for attaching said plate to the proximal tibia,
   said head portion oriented transverse to said shaft portion and extending on only said posterior side of said shaft portion,
   said shaft portion having a laterally straight proximal portion and a laterally straight distal portion that are angled relative to each other at an angle of 168° to 173°, a center of said angle located along said longitudinal axis of said shaft portion and positioned 42 mm to 50 mm from said proximal row in said head portion, and a center of an anteriormost screw hole of said first plurality of screw holes in said head portion being displaced in a posterior direction from said anterior side of said distal portion of said shaft portion by 10 mm to 12 mm such that said center of said anteriormost screw hole is located on a posterior side of said longitudinal axis of said shaft portion, and
   said head portion having a frontal offset relative to said distal shaft portion by 14 mm to 20 mm.

2. A periarticular bone plate according to claim 1, wherein: said first plurality of screw holes are internally threaded such that the threads of said first plurality of screw holes define respective screw hole axes for said first plurality of screw holes along which said first plurality of screw holes are adapted to secure the fasteners to said plate.

3. A periarticular bone plate according to claim 2, wherein: said screw holes of said first plurality each include a recess thereabout.

4. A periarticular bone plate according to claim 1, wherein: said proximal and distal rows are parallel.

5. A periarticular bone plate according to claim 1, wherein: said second plurality of screw holes are internally threaded such that the threads of said second plurality screw holes define respective screw hole axes for said second plurality of screw holes along which said second plurality of screw holes are adapted to secure the fasteners to said plate.

6. A periarticular bone plate according to claim 1, wherein: said head portion includes a scalloped contour along a proximal edge and along said posterior side.

7. A periarticular bone plate according to claim 6, wherein: said head portion has a straight anterior side.

8. A periarticular bone plate according to claim 1, further comprising:
   the fastener.

9. A periarticular bone plate according to claim 8, wherein: said fastener is a locking fastener having a head with threads and a shaft.

10. A periarticular bone plate according to claim 8, wherein:
    said fastener is a non-locking compressive fastener having a non-threaded head and a shaft with bone-engaging threads.

11. A periarticular bone plate for use with bone fasteners for stabilizing a fracture of the proximal tibia, comprising:
    a shaft portion and a head portion unitary with the shaft portion, the shaft and head portions having a bone contacting bottom surface, an opposite top surface, an anterior side, and a posterior side,
    said head portion defining a first plurality of screw holes configured in a proximal row of at least three screw holes and a distal row of at least three screw holes, and said shaft portion defining a second plurality of screw holes longitudinally displaced relative to a longitudinal axis of said shaft, said first and second plurality of screw holes screw holes extending between said top and bottom surfaces for receiving fasteners for attaching said plate to the proximal tibia,
    said head portion oriented transverse to said shaft portion and extending on only said posterior side of said shaft portion, and said head portion including a hole defined by a first path sized to guide a K-wire generally along a first axis extending through said top and bottom surfaces, and a second path having a second axis extending inward from a proximal edge to intersect said first axis at a point of intersection, wherein from said first path to said proximal edge said second path is located under said top surface,
    said shaft portion having a laterally straight proximal portion and a laterally straight distal portion that are angled relative to each other at an angle of 168° to 173°, a center of said angle located along said longitudinal axis of shaft portion and positioned 42 mm to 50 mm from said proximal row in said head portion, and a center of an anteriormost screw hole of said first plurality of screw holes in said head portion being displaced from said anterior side of said distal portion of said shaft portion by 10 mm to 12 mm, and
    said head portion having a frontal offset relative to said distal shaft portion by 14 mm to 20 mm.

12. A periarticular bone plate according to claim 11, wherein:
    from said first path to said proximal edge, said second path extends entirely between said top and bottom surfaces.

13. A periarticular bone plate for use with bone fasteners for stabilizing a fracture of the proximal tibia, comprising:
    a shaft portion and a head portion unitary with the shaft portion, the shaft and head portions having a bone contacting bottom surface, an opposite top surface, an anterior side, and a posterior side,
    said head portion defining a first plurality of screw holes, and said shaft portion defining a second plurality of screw holes longitudinally displaced relative to a longitudinal axis of said shaft, said first and second plurality of screw holes extending between said top and bottom surfaces for receiving fasteners for attaching said plate to the proximal tibia, said head portion oriented transverse to said shaft portion and extending on only said posterior side of said shaft portion, and said head portion includes a hole defined by a first path sized to guide a K-wire generally along a first axis extending through said top and bottom surfaces, and a second path having a second axis extending inward from a proximal edge to intersect said first axis at a point of intersection, wherein from said first path to said proximal edge said second path is located under said top surface, said shaft portion having a laterally straight proximal portion and a laterally straight distal portion that are angled relative to each other at an angle of 168° to 173°, a center of said angle located along said longitudinal axis of shaft portion and positioned 42 mm to 50 mm from a proximalmost screw hole in said head portion, and said head portion having a frontal offset relative to said distal shaft portion.

14. A periarticular bone plate according to claim 13, wherein:

from said first path to said proximal edge, said second path extends entirely between said top and bottom surfaces.

15. A periarticular bone plate according to claim 13, wherein:

said frontal offset is 14 mm to 20 mm.

16. A periarticular bone plate according to claim 13, wherein:

said first plurality of screw holes are arranged in proximal and distal rows.

17. A periarticular bone plate according to claim 13, wherein:

said first plurality of screw holes are internally threaded such that the threads of said first plurality of screw holes define respective screw hole axes for said first plurality of screw holes along which said first plurality of screw holes are adapted to secure the fasteners to said plate.

18. A periarticular bone plate according to claim 13, wherein:

said second plurality of screw holes are internally threaded such that the threads of said second plurality screw holes define respective screw hole axes for said second plurality of screw holes along which said second plurality of screw holes are adapted to secure the fasteners to said plate.

19. A periarticular bone plate according to claim 13, wherein:

said head portion includes a scalloped contour along a proximal edge and along said posterior side, and a straight anterior side.

* * * * *

UNITED STATES PATENT AND TRADEMARK OFFICE
CERTIFICATE OF CORRECTION

| | | |
|---|---|---|
| PATENT NO. | : 8,262,707 B2 | Page 1 of 1 |
| APPLICATION NO. | : 12/183115 | |
| DATED | : September 11, 2012 | |
| INVENTOR(S) | : Huebner et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 918 days.

Signed and Sealed this
Twenty-fourth Day of June, 2014

Michelle K. Lee
*Deputy Director of the United States Patent and Trademark Office*